(12) United States Patent
Li et al.

(10) Patent No.: US 7,047,076 B1
(45) Date of Patent: May 16, 2006

(54) INVERTED-F ANTENNA CONFIGURATION FOR AN IMPLANTABLE MEDICAL DEVICE

(75) Inventors: Zhifang Li, Blaine, MN (US); Prashant Rawat, Blaine, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 255 days.

(21) Appl. No.: 10/808,060

(22) Filed: Mar. 24, 2004

Related U.S. Application Data

(63) Continuation-in-part of application No. 10/634,233, filed on Aug. 5, 2003, now Pat. No. 6,809,701, and a continuation-in-part of application No. 10/744,943, filed on Dec. 22, 2003, which is a continuation of application No. 10/252,494, filed on Sep. 23, 2002, now Pat. No. 6,614,406, which is a continuation of application No. 09/921,653, filed on Aug. 3, 2001, now Pat. No. 6,456,256.

(51) Int. Cl.
*A61N 1/06* (2006.01)

(52) U.S. Cl. ............................ 607/36; 607/32; 607/60; 128/903; 343/718

(58) Field of Classification Search .................. 607/32, 607/36, 156, 60; 343/718, 873, 845, 172; 128/903; 340/572, 7; 118/723 I
See application file for complete search history.

(56) References Cited

U.S. PATENT DOCUMENTS

| | | | |
|---|---|---|---|
| 4,441,498 A | 4/1984 | Nordling | |
| 4,542,535 A | 9/1985 | McQualkin | |
| 4,556,063 A | 12/1985 | Thompson et al. | |
| 4,562,841 A | 1/1986 | Brockway et al. | |
| 4,851,855 A * | 7/1989 | Tsukamoto et al. | 349/700 MS |
| 4,944,299 A | 7/1990 | Silvian | |
| 5,058,581 A | 10/1991 | Silvian | |
| 5,113,869 A | 5/1992 | Nappholz et al. | |
| 5,127,404 A | 7/1992 | Wyborny et al. | |
| 5,314,453 A | 5/1994 | Jeutter | |
| 5,337,756 A | 8/1994 | Barbier et al. | |
| 5,342,408 A | 8/1994 | deCoriolis et al. | |
| 5,354,319 A | 10/1994 | Wyborny et al. | |
| 5,517,676 A * | 5/1996 | Sekine et al. | 455/575.5 |
| 5,562,713 A | 10/1996 | Silvian | |
| 5,579,876 A | 12/1996 | Adrian et al. | |
| 5,626,630 A | 5/1997 | Markowitz et al. | |
| 5,683,432 A | 11/1997 | Goedeke et al. | |
| 5,735,887 A | 4/1998 | Barreras, Sr. et al. | |
| 5,766,232 A | 6/1998 | Grevious et al. | |
| 5,861,019 A | 1/1999 | Sun et al. | |

(Continued)

OTHER PUBLICATIONS

Massey, P. J.; "Fabric Antennas for Mobile Telephony Integrated within Clothing," Phillips Research Laboratories, Redhill, UK; 4 pages.

(Continued)

*Primary Examiner*—Robert E. Pezzuto
*Assistant Examiner*—Deborah Malamud
(74) *Attorney, Agent, or Firm*—Faegre & Benson LLP

(57) ABSTRACT

Systems, methods and devices facilitating wireless communication with a medical device employ an antenna that provides for increased efficiency, broader bandwidth, and/or improved impedance matching characteristics. In some cases, this antenna is an inverted-f antenna, and in one particular case, the antenna is a non-planar inverted-f antenna. In some cases, the antenna is disposed within a dielectric housing extending along a portion of the side of the medical device.

36 Claims, 9 Drawing Sheets

U.S. PATENT DOCUMENTS

| | | |
|---|---|---|
| 5,862,803 A | 1/1999 | Besson et al. |
| 5,957,854 A | 9/1999 | Besson et al. |
| 6,009,350 A | 12/1999 | Renken |
| 6,115,583 A | 9/2000 | Brummer et al. |
| 6,115,636 A | 9/2000 | Ryan |
| 6,141,584 A | 10/2000 | Rockwell et al. |
| 6,169,925 B1 | 1/2001 | Villaseca et al. |
| 6,240,317 B1 | 5/2001 | Villaseca et al. |
| 6,434,429 B1 | 8/2002 | Kraus et al. |
| 6,456,256 B1 | 9/2002 | Amundson et al. |
| 6,466,810 B1 | 10/2002 | Ward et al. |
| 6,574,510 B1 | 6/2003 | Von Arx et al. |
| 6,602,201 B1 | 8/2003 | Hepp et al. |
| 6,609,023 B1 | 8/2003 | Fischell et al. |
| 6,614,406 B1 | 9/2003 | Amundson et al. |
| 6,622,043 B1 | 9/2003 | Kraus et al. |
| 6,622,045 B1 | 9/2003 | Snell et al. |
| 6,635,014 B1 | 10/2003 | Starkweather et al. |
| 6,636,769 B1 | 10/2003 | Govari et al. |
| 6,638,231 B1 | 10/2003 | Govari et al. |
| 6,644,321 B1 | 11/2003 | Behm |
| 6,644,322 B1 | 11/2003 | Webb |
| 6,647,299 B1 | 11/2003 | Bourget |
| 6,648,821 B1 | 11/2003 | Lebel et al. |
| 6,648,823 B1 | 11/2003 | Thompson |
| 6,650,941 B1 | 11/2003 | Ferek-Petric |
| 6,650,944 B1 | 11/2003 | Goedeke |
| 6,658,283 B1 | 12/2003 | Bornzin et al. |
| 6,658,300 B1 | 12/2003 | Govari et al. |
| 6,675,045 B1 * | 1/2004 | Mass et al. .................. 607/32 |
| 2002/0013613 A1 | 1/2002 | Haller et al. |
| 2002/0019586 A1 | 2/2002 | Teller et al. |
| 2002/0019606 A1 | 2/2002 | Lebel et al. |
| 2002/0026223 A1 | 2/2002 | Riff et al. |
| 2002/0029321 A1 | 3/2002 | Beetz et al. |
| 2002/0058906 A1 | 5/2002 | Lebel et al. |
| 2002/0065454 A1 | 5/2002 | Lebel et al. |
| 2002/0065509 A1 | 5/2002 | Lebel et al. |
| 2002/0065539 A1 | 5/2002 | Von Arx et al. |
| 2002/0065540 A1 | 5/2002 | Lebel et al. |
| 2002/0072783 A1 | 6/2002 | Goedeke et al. |
| 2002/0077553 A1 | 6/2002 | Govari et al. |
| 2002/0077671 A1 | 6/2002 | Govari et al. |
| 2002/0077672 A1 | 6/2002 | Govari et al. |
| 2002/0077673 A1 | 6/2002 | Penner et al. |
| 2002/0082665 A1 | 6/2002 | Haller et al. |
| 2002/0087203 A1 | 7/2002 | Schmitt et al. |
| 2002/0091416 A1 | 7/2002 | Wassmund et al. |
| 2002/0099412 A1 | 7/2002 | Fischell et al. |
| 2002/0099424 A1 | 7/2002 | Ferek-Petric |
| 2002/0103514 A1 | 8/2002 | Abrahamson |
| 2002/0111539 A1 | 8/2002 | Cosentino et al. |
| 2002/0116032 A1 | 8/2002 | Ferek-Petric |
| 2002/0123672 A1 | 9/2002 | Christophersom et al. |
| 2002/0123673 A1 | 9/2002 | Webb et al. |
| 2002/0123776 A1 | 9/2002 | Von Arx et al. |
| 2002/0126036 A1 | 9/2002 | Flaherty et al. |
| 2002/0143372 A1 | 10/2002 | Snell et al. |
| 2002/0147388 A1 | 10/2002 | Mass et al. |
| 2002/0151770 A1 | 10/2002 | Noll, III et al. |
| 2002/0156504 A1 | 10/2002 | Chen et al. |
| 2002/0173830 A1 | 11/2002 | Starkweather et al. |
| 2002/0188215 A1 | 12/2002 | Ferek-Petric |
| 2002/0188773 A1 | 12/2002 | Augustijn et al. |
| 2002/0190905 A1 | 12/2002 | Flint et al. |
| 2002/0193839 A1 | 12/2002 | Cho et al. |
| 2002/0193846 A1 | 12/2002 | Pool et al. |
| 2002/0198462 A1 | 12/2002 | Begemann |
| 2003/0006898 A1 | 1/2003 | Herzberg |
| 2003/0009204 A1 | 1/2003 | Amundson et al. |
| 2003/0022637 A1 | 1/2003 | Hirota |
| 2003/0023175 A1 | 1/2003 | Arzbaecher et al. |
| 2003/0025645 A1 | 2/2003 | Amundson et al. |
| 2003/0028226 A1 | 2/2003 | Thompson et al. |
| 2003/0041866 A1 | 3/2003 | Linberg et al. |
| 2003/0114896 A1 | 6/2003 | Boute et al. |
| 2003/0114897 A1 | 6/2003 | Von Arx et al. |
| 2003/0122718 A1 | 7/2003 | Fang et al. |
| 2003/0139778 A1 | 7/2003 | Fischell et al. |
| 2003/0144718 A1 | 7/2003 | Zeijlemaker |
| 2003/0149423 A1 | 8/2003 | Fischell et al. |
| 2003/0176933 A1 | 9/2003 | Lebel et al. |
| 2003/0177031 A1 | 9/2003 | Malek |
| 2003/0195396 A1 | 10/2003 | Scarantino et al. |
| 2003/0195584 A1 | 10/2003 | Von Arx et al. |
| 2003/0199939 A1 | 10/2003 | Schmitt et al. |
| 2003/0204216 A1 | 10/2003 | Ries et al. |
| 2003/0212441 A1 | 11/2003 | Starkweather et al. |
| 2003/0216793 A1 | 11/2003 | Karlsson et al. |
| 2003/0222823 A1 | 12/2003 | Flint et al. |
| 2004/0027306 A1 | 2/2004 | Amundson et al. |
| 2005/0055068 A1 | 3/2005 | Von Arx et al. |
| 2005/0134520 A1 | 6/2005 | Rawat et al. |

OTHER PUBLICATIONS

Chen, Zhi Ning et al.; "A New Inverted F Antenna with a Ring Dielectric Resonator," IEEE Transactions on Vehicular Technology, vol. 48, No. 4, (Jul. 1999); pp. 1029-1032.

Hong, Wonbin; "Design of Small Inverted F Antenna for Low Frequencies," Department of Electrical and Computer Enginerring, Purdue University, 5 pages.

"Inverted F Antenna," http://www.qsl.net/kb7qhc/antenna/Inverted%20F; (Dec. 4, 2003); 2 pages.

"Film Type Inverted F Antenna," Honda Tsushin Kogyo Co., Ltd., Honda connectors; (Jun. 17, 2003); pp. 1-11.

* cited by examiner

US 7,047,076 B1

INVERTED-F ANTENNA CONFIGURATION FOR AN IMPLANTABLE MEDICAL DEVICE

CROSS-REFERENCE TO RELATED APPLICATION(S)

The present application is a continuation-in-part of U.S. patent application Ser. No. 10/744,943, entitled "Radio Frequency Antenna in a Header of an Implantable Medical Device," filed Dec. 22, 2003 by Rawat et al.; and a continuation-in-part of U.S. patent application Ser. No. 10/634,233 entitled "Circumferential Antenna for an Implantable Medical Device," filed Aug. 5, 2003, now U.S. Pat. No. 6,809,701 which is a continuation of Ser. No. 10/252,494, now U.S. Pat. No. 6,614,406, filed Sep. 23, 2002, which is a continuation of Ser. No. 09/921,653, now U.S. Pat. No. 6,456,256, filed Aug. 3, 2001. Further, the present application is related to U.S. patent application Ser. No. 10/454,013 entitled "Telemetry Apparatus and Method for an Implanatable Medical Device," filed Jun. 3, 2003 by Von Arx et al., which is a continuation of U.S. Pat. No. 6,574,510, filed Nov. 30, 2000. All of the aforementioned patents and patent applications are incorporated herein by reference in their entirety.

TECHNICAL FIELD

The present invention is related to implantable medical devices such as cardiac rhythm management devices, and in particular to systems and methods for wireless communication to and from such devices.

BACKGROUND

Various implantable medical devices, such as implantable cardioverter/defibrillators and pacemakers, include wireless communication capability. This wireless communication capability allows for communication with the implantable medical device after the device is implanted within a patient. Thus, information can be provided to or obtained from an implanted medical device without requiring the patient to undergo a post-implant surgical procedure.

In an exemplary scenario, a clinician uses an external programmer placed outside the patient's body and in near proximity to an implanted pacemaker to transmit pacing mode and other operating characteristics to the pacemaker. As another example, information can be transmitted from the implanted pacemaker and received by the external programmer operating in close proximity to the pacemaker.

Various telemetry systems for transmitting to or from an implanted medical device have utilized radio-frequency energy as the transmission medium. An exemplary telemetry system for an external programmer and a cardiac pacemaker is described in U.S. Pat. No. 4,562,841 (hereinafter the "'841 patent"). The '841 patent is assigned to Cardiac Pacemakers, Inc., and the '841 patent is incorporated herein in its entirety for all purposes. A radio-frequency carrier is modulated with digital information, typically by amplitude shift keying where the presence or absence of pulses in the signal constitutes binary symbols or bits. The external programmer transmits and receives the radio signal with an antenna incorporated into a wand, which can be positioned in proximity to the implanted medical device. The implanted device also generates and receives the radio signal by means of an antenna associated with the device.

For communication to take place in typical telemetry systems, antenna inefficiencies, as well as other limitations, required placement of the wand in near proximity to and/or within a narrow alignment window. This requirement is inconvenient for a clinician or patient, and limits situations in which communication with an implanted device can take place. Thus, there is a need in the art for improved systems and methods for wireless communications with medical devices.

SUMMARY

The present invention provides various systems and methods for wireless communication with a medical device. Some embodiments of the present invention include an antenna that provides for increased efficiency, broader bandwidth, and/or improved impedance matching characteristics. Other embodiments provide these and/or other advantages as will be appreciated by those of ordinary skill in the art upon reading this disclosure. For example, various embodiments of the present invention provide for increased range between an implanted medical device and an external programmer, and/or increased flexibility in aligning an external programmer in relation to an implanted medical device.

The present invention, according to one embodiment, is an implantable medical device including a housing surrounding at least one circuit, an inverted-f antenna extending along the housing, and a coating covering at least a portion of the housing and at least a portion of the inverted-f antenna. The at least one circuit is communicably coupled to the inverted-f antenna.

The present invention, according to another embodiment, is a method for interacting with an implanted medical device. The method includes providing an external programmer in relation to a deployed medical device, disposed within a living being. The deployed medical device includes a housing surrounding at least one electrical circuit, wherein the housing includes a header, and an antenna, wherein the antenna includes a feed line, wherein the at least one electrical circuit is electrically coupled to the feed line, and wherein a length of the antenna extends along an outer surface of the housing away from the header. The method further includes performing a function selected from a group consisting of: receiving information from the deployed medical device and providing information to the deployed medical device.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
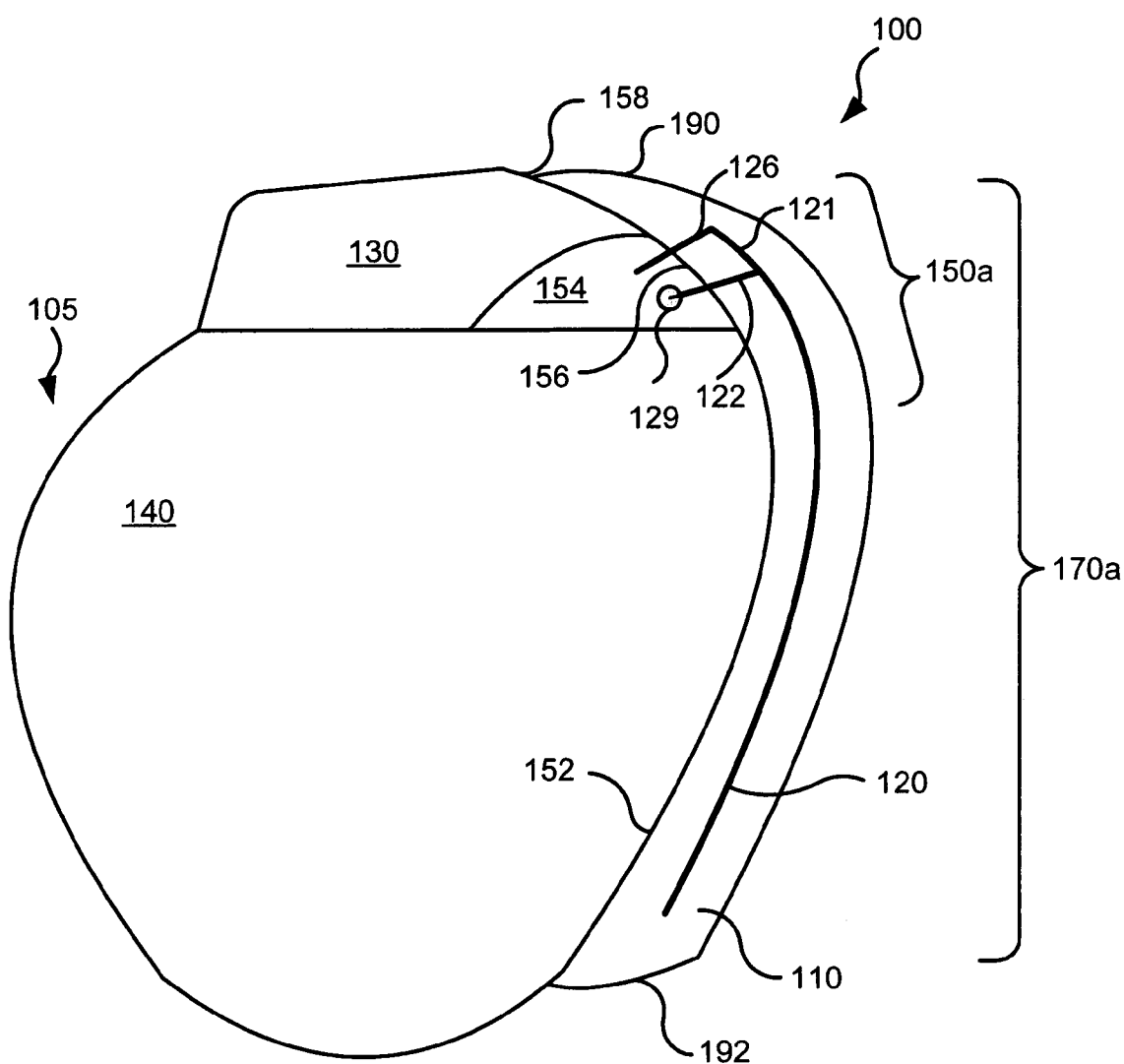
FIGS. 1A–1E illustrates an exemplary medical device including an antenna in accordance with several embodiments of the present invention.

The present invention provides various systems and methods for wireless communication with a medical device. In some embodiments of the present invention, the wireless communication is radio-frequency (RF) based communications performed using one or more antennas that provide increased efficiency, broader bandwidth, or improved impedance matching characteristics. Various embodiments of the present invention also provide for different carrier frequencies transmitted from a single antenna. Thus, for example, a different carrier frequency can be utilized when a device is used in different geopolitical regions. In one particular embodiment, the quarter wavelength is defined based on a first frequency compatible with one geopolitical region, and the half wavelength is defined based on a second frequency compatible with another geopolitical region. Other wavelength integrals and/or combinations thereof can also be used in accordance with other embodiments of the present invention.

Various medical devices incorporate RF telemetry components for communication between the device and an external transmitter or receiver (hereinafter an "external programmer"). Such RF communication relies upon electromagnetic coupling between one antenna associated with the medical device and another associated with an external programmer. In inductive telemetry systems, the electromagnetic field produced by a transmitting antenna decreases as a function of distance to the sixth power. To work properly, an external programmer can be located in close proximity to the medical device, and within a narrow alignment window extending in relation to the medical device. Various embodiments of the present invention facilitate RF communications at increased distances, and/or over a wider alignment window referred to herein as a field of view (FOV).

Where embodiments of the present invention incorporate RF antennas, a short discussion of operation and design characteristics associated with RF antennas is provided. Additional antenna literature may also be consulted by one of ordinary skill in the art in determining the full extent of the disclosure provided herein. A time-varying electrical current flowing in an antenna produces a corresponding electromagnetic field configuration that propagates through space in the form of electromagnetic waves. The total field configuration produced by an antenna can be decomposed into a far-field component, where the magnitudes of the electric and magnetic fields vary inversely with distance from the antenna, and a near-field component with field magnitudes varying inversely with higher powers of the distance. The field configuration in the immediate vicinity of the antenna is primarily due to the near-field component, also known as the induction field, while the field configuration at greater distances is due solely to the far-field component, also known as the radiation field. The near-field is a reactive field in which energy is stored and retrieved but results in no net energy outflow from the antenna unless a load is present in the field, coupled either inductively or capacitively to the antenna. The far-field, on the other hand, is a radiating field that carries energy away from the antenna regardless of the presence of a load in the field. This energy loss appears to a circuit driving the antenna as a resistive impedance which is known as the radiation resistance. If the frequency of the RF energy used to drive an antenna is such that the wavelength of electromagnetic waves propagating therein is much greater than the length of the antenna, a negligible far-field component is produced.

A dipole antenna, for example, is a center-driven conductor that has a length equal to half the wavelength of the driving signal. Such a dipole antenna can be made of two lengths of metal arranged end to end with the cable from a transmitter/receiver feeding each length of the dipole in the middle. An efficiently radiating resonant structure is formed if each length of metal in the dipole is a quarter-wavelength long, so that the combined length of the dipole from end to end is a half-wavelength. A shorter antenna can produce a similar field configuration by utilizing a ground plane to reflect electromagnetic waves emitted by the antenna and thereby produce an image field. A monopole antenna is a conductor with a length equal to one-quarter the wavelength of the driving signal situated with respect to a reflecting ground plane so that the total emitted and reflected field configuration resembles that of the dipole antenna. As an example, a carrier frequency of one GHz can be chosen which corresponds to a wavelength of approximately thirty cm in free space. Thus, in free space a half-wavelength dipole antenna would optimally be approximately fifteen cm long, and a quarter-wavelength monopole antenna would optimally have a length approximately seven and one half cm in length. Additional information about antennas and the theory of antenna operation is provided in C. A. Balanis, "Antenna Theory: Analysis and Design", second edition, John Wiley & Sons, 1997. The entirety of the aforementioned reference is incorporated herein by reference for all purposes.

Where the device is to be implanted in, for example, a human body, the permittivity of the human body tissues can be considered. The optimal antenna length is approximately proportional to the inverse of square root of the permittivity of the surrounding media. The human body tissues vary significantly from person to person, and their average permittivity can be in a range from about four through fifty-five. Further, in addition to the permittivity of the human body, a dielectric housing surrounding the antenna can have a major impact on an optimal length of the antenna. Thus, the optimum antenna length in a human body would be much shorter than for that of a corresponding antenna in free space.

FIGS. 1A–1E show various views of an exemplary medical device 100, including an antenna 170a in accordance with some embodiments of the present invention. The medical device 100 can be any number of devices including both implantable and non-implant type medical devices. As just some examples, implantable medical devices can provide for cardiac rhythm management, physiological monitoring, drug delivery, and/or neuromuscular stimulation. Exemplary cardiac rhythm management devices include pacemakers, implantable cardioverter/defibrillators, and cardiac resynchronization therapy devices. While various aspects of the present invention can be applied to a number of medical devices, for discussion purposes the medical device 100 is illustrated and described as a cardiac pacemaker.

The medical device 100 includes a housing 105 comprised of a header 130 and a body 140. The housing 105 can be formed of an electrically conductive material, such as metal, that provides an electrically shielded compartment for electronic circuitry maintained within the housing 105. Such electronic circuitry provides the particular functionality of a given medical device. As just some examples, the electronic circuitry can include a modulation and/or demodulation circuit electrically coupled to the antenna 170*a* and operable to transmit and/or receive RF communications.

As depicted, the antenna 170*a* is an inverted-f antenna with a transmitting length 120 extending along a side 152 of body 140. Antenna 170*a* further includes a feed line 122 that passes through a feed-through 129 where it is electrically coupled to electronic circuitry within the housing 105. Further, the antenna 170*a* includes a shunt arm 121 that extends along a side 156 of the header 130 and that is electrically coupled to a conductive portion of the header 130 by a connector leg 126. A side 158 of the header 130 continues beyond the antenna 170*a*.

While the feed-through 129 is shown in the header 130, in other cases, the feed-through 129 can be in an antenna radome outside of the header or some other portion of body 140. Further, in various embodiments the connector leg 126 can be electrically coupled at an electrically conductive portion of the header 130 or the body 140, depending upon the desired attachment location of the antenna 170. Additionally, it should be recognized that while an inverted-f antenna is illustrated, the antenna 170 can be any conductive structure capable of efficiently radiating electromagnetic energy, as are known to those of skill in the art. Thus, the antenna 170 can be comprised of a rod, a wire, a patch, or a loop. In some cases, a wire antenna is desirable as it simplifies manufacturing, and increases volumetric efficiency. Further, a wire antenna tends to have a near isotropic radiation pattern in the horizontal plane with fewer null locations as compared with other types of antennas. In some cases, the antenna 170 is constructed of one or more materials including, but not limited to, platinum, iridium, stainless steel, or combinations thereof such as platinum-iridium.

An external antenna on a medical device may require special deployment procedures to limit the possibility of breaking or deforming the antenna 170. Thus, in some embodiments of the present invention, the antenna 170 is disposed within a dielectric housing 110 (also referred to herein as a dielectric compartment). The dielectric housing 110 can be formed of a dielectric material coating the antenna 170 in such a way that the transmitting length 120 is isolated a distance from the housing 105, and the antenna 170 is isolated from environmental conditions into which the medical device 100 is implanted or deployed. The dielectric housing 110 can be formed of any type of dielectric material, and where the medical device 100 is to be implanted in a human body, choice of the dielectric material may include biocompatibility considerations. Some examples of dielectric materials include polymers such as parylene, ecothane, tecothane, thermoplastic urethane, polytetrafluooethylene (PTFE), expanded polytetrafluooethylene (ETFE), and/or polytheretherketone (PEEK). Various possible coatings are disclosed in the previously discussed patent applications that are incorporated herein by reference for all purposes.

Further, in some cases, one or more dielectric materials are used as a coating placed over the exterior of the medical device 100. In one particular case, the dielectric material is a polyurethane resin used in the header portion of cardiac rhythm management devices where the various therapy leads connect to the device.

In embodiments where the medical device 100 is to be implanted in a patient, it may be desirable for medical device 100 to be as small as possible. This limited size may constrain the carrier frequencies that can be used if a quarter-wavelength monopole or half-wavelength dipole antenna is to be embedded with the device. Various embodiments of the present invention seek a tradeoff between device size and desired carrier frequencies. Further, sharp edges may need to be avoided for patient comfort. Thus, for example, edges 190, 192 of dielectric housing 110 may be rounded, and/or brought into conformity with edges of housing 105 such that protrusions are avoided.

One particular embodiment of the invention includes a dielectric housing 110 that extends between approximately thirty-five to one hundred five mils from the edge of housing 105. This allows for a distance of thirty to one hundred mils between the transmitting length 120 of the antenna 170 and the body 140. In one particular case, the distance is seventy-five mils between the transmitting length 120 and the body 140. In another particular case, the distance between the antenna 170 and the body 140 is between one and one half, and three millimeters. The distances between the transmitting length 120 and the body 140 allow for substantially monopole operation of the antenna 170, and yet maintains a small size of the medical device 100. An ideal monopole antenna, i.e., an antenna extending perpendicular from the side of the housing 105, may not be possible at a desired frequency and without creating a protrusion that would be biologically irritating and/or otherwise incompatible with the size of the medical device. Thus, although the aforementioned dimensions do not offer an ideal monopole antenna, they do offer sufficiently monopolar characteristics where the transmission line (i.e., the transmission line comprised of the transmitting length 120 extending along the housing 105) characteristics are minimized. These transmission line effects can be reduced by careful adjustment, or tuning, of the shunt arm 121. More specifically, the length of the shunt arm 121 can be adjusted to match the impedance looking down the transmission line, and considering the connection to circuitry within the housing 105, as is known in the art.

A cutout section 154 is provided to illustrate the connection between antenna 170*a* and housing 105. Further, a section 150*a* is also identified for correlation between FIG. 1A and FIGS. 1B–1C.

Figure 1B:
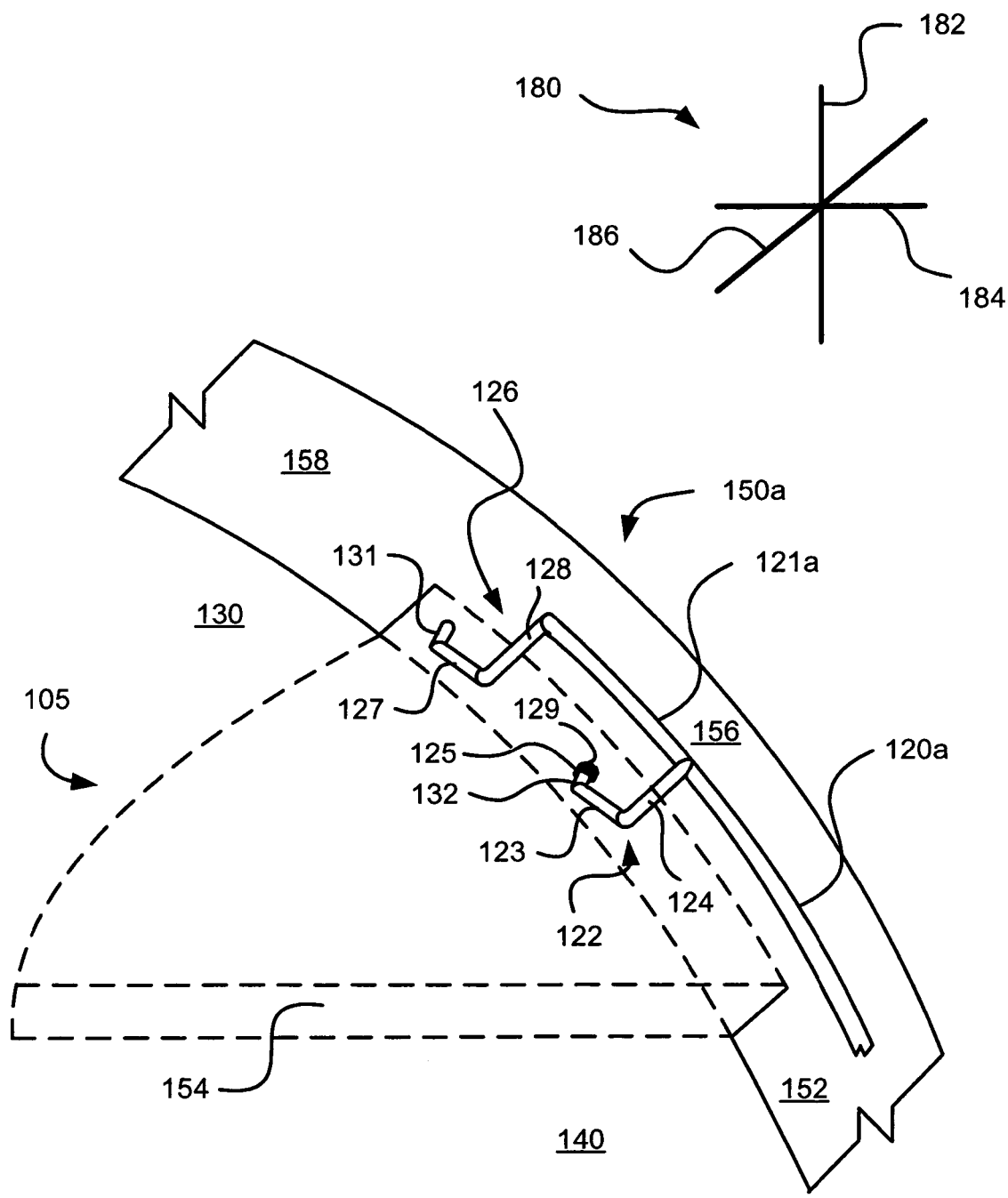

FIG. 1B shows a close-up view of the section 150*a* and the cutout 154. As the antenna 170*a* is a non-planar inverted-f antenna, an axis 180 showing an x-axis 184, a y-axis 182, and a z-axis 186 is provided for description purposes. The transmitting length 120*a* extends in the x-y plane along the side 152, and connects with the shunt arm 121*a* and the feed line 122. The feed line 122 includes a section 124 extending in the y-z plane, a section 123 extending in the x-y plane, and a section 132 extending in the y-z plane. The section 132 of the feed line 122 is surrounded by a glass/metal sleeve 125 that attaches to the housing 105 at the feed-through 129, and hermetically seals the interior of housing 105 from a surrounding environment. The glass shell of the sleeve 125 insulates the feed line 122 from the housing 105. Section 132 of the feed line 122 extends through the housing 105 and is electrically coupled to electronic circuitry within the housing 105.

As shown in FIG. 1B, the shunt arm 121*a* is electrically coupled to the housing 105 via the connector leg 126. The connector leg 126 includes a section 128 extending in the y-z plane, a section 127 extending in the x-y plane, and a section 131 extending in the y-z plane. The section 131 is electrically coupled to the housing 105.

Figure 1C:
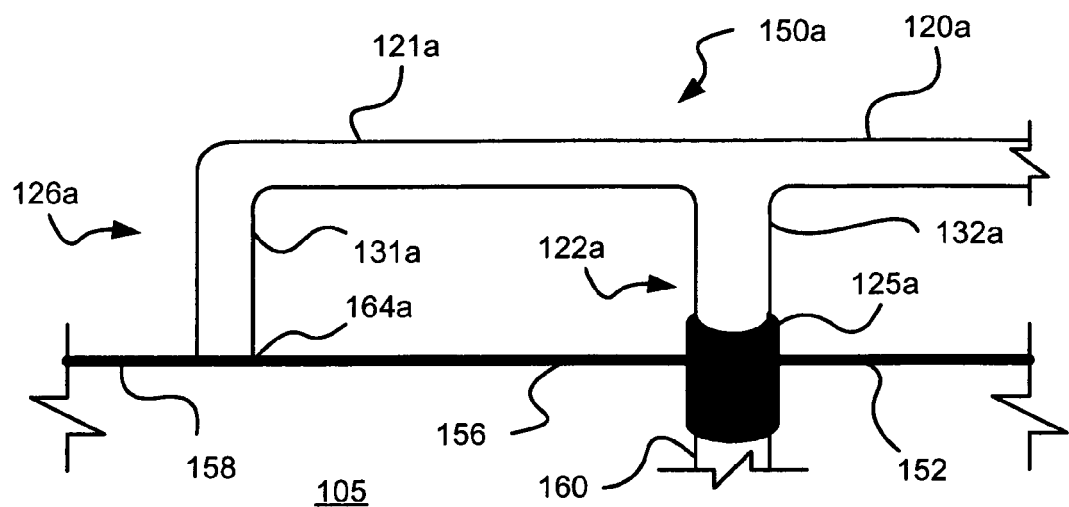
Figure 1D:
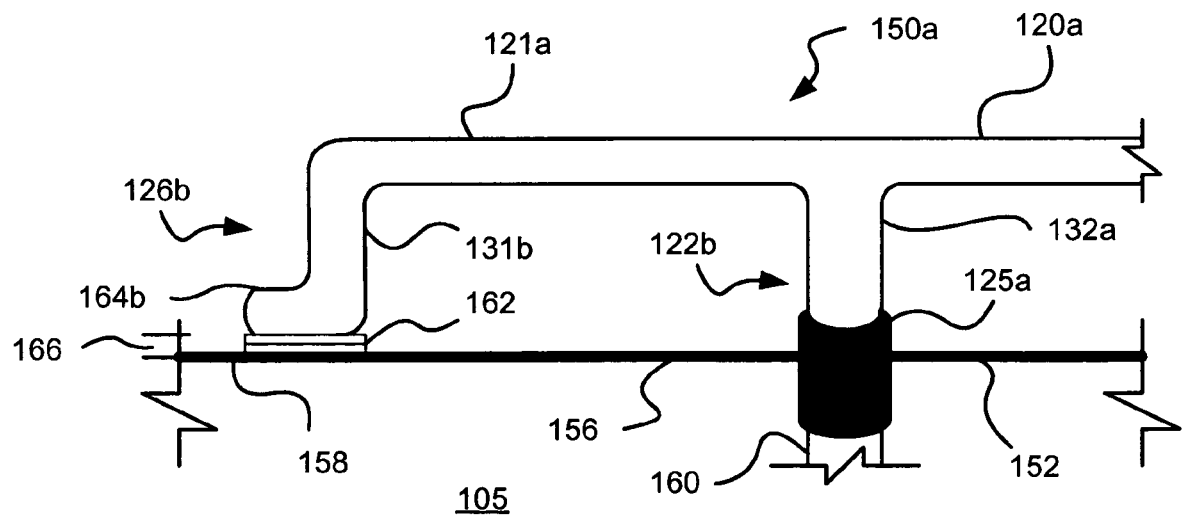

FIGS. 1C and 1D are detailed cross sectional diagrams of the section 150 depicting different embodiments of the present invention. As depicted in FIG. 1C, the section 131*a* of the connector leg 126*a* is mechanically coupled to the exterior surface of the housing 105 at a location 164*a*. Further, a section 160 of the feed line 122*a* extending into the housing 105 is shown.

In FIG. 1D, the section 131*b* of the connector leg 126*b* is capacitively coupled to the exterior of the housing 105 at a location 164*b*. The capacitive coupling is formed between a section of the connector leg 126*b* laid parallel to the surface of the housing 105, and separated by a thickness 166 of a dielectric material 162. In one case, the shunt arm 121*a* is covered by a thin dielectric film such as, for example, parylene, that acts as the dielectric material 162 and defines a thickness 166. In some cases, the portion of the section 131*a* that is laid parallel to the side 156 is a flattened plate with a greater surface area capable of increasing the capacitive coupling.

Capacitively coupling the connector leg 126 to the housing 105 allows the transmitting length 120 of the antenna 170 to double as a therapy lead or secondary electrode. Thus, in addition to transmitting RF radiation, the transmitting length 120 can be used to pass low frequency electrical signals. As just one example, the transmitting length 120 may be utilized as one electrode in a three electrode group used for generating an electrocardiogram signal, such that a physician need not connect externally to a patient's chest. Further examples and discussion of such therapy leads is provided in U.S. patent application Ser. No. 10/454,013 entitled "Telemetry Apparatus and Method for an Implantable Medical Device", and filed Jun. 3, 2003 by Von Arx et. Al, which is incorporated herein by reference in its entirety.

Figure 1E:
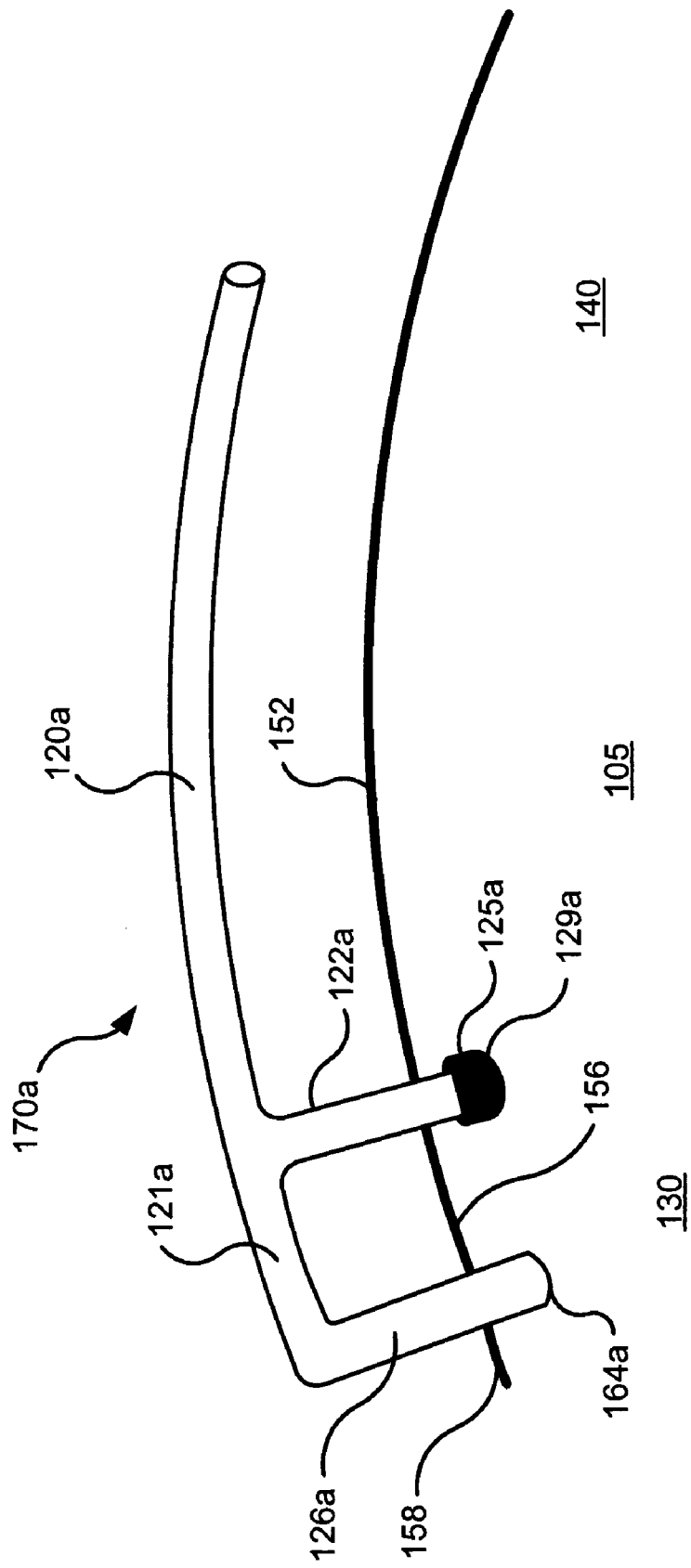

FIG. 1E is an overall cross-sectional view of the antenna 170*a*. As previously discussed, many different antenna types and/or configurations thereof can be used in accordance with different embodiments of the present invention. In one particular embodiment, the distance along shunt arm 121*a* from the outer edge of connector leg 126*a* to the closer edge of feed line 122*a* is six millimeters, and the distance along transmitting length 120*a* from the same closer edge of feed line 122*a* to the end of transmitting length 120*a* is 61.45 millimeters. The diameter of transmitting length 120*a* is 0.9 millimeters, and the distance from transmitting length 120*a* to side 152 of body 140 is 25.45 millimeters. These dimensions can be used for a straight-wire 916 MHz inverted-F antenna.

Figure 2A:
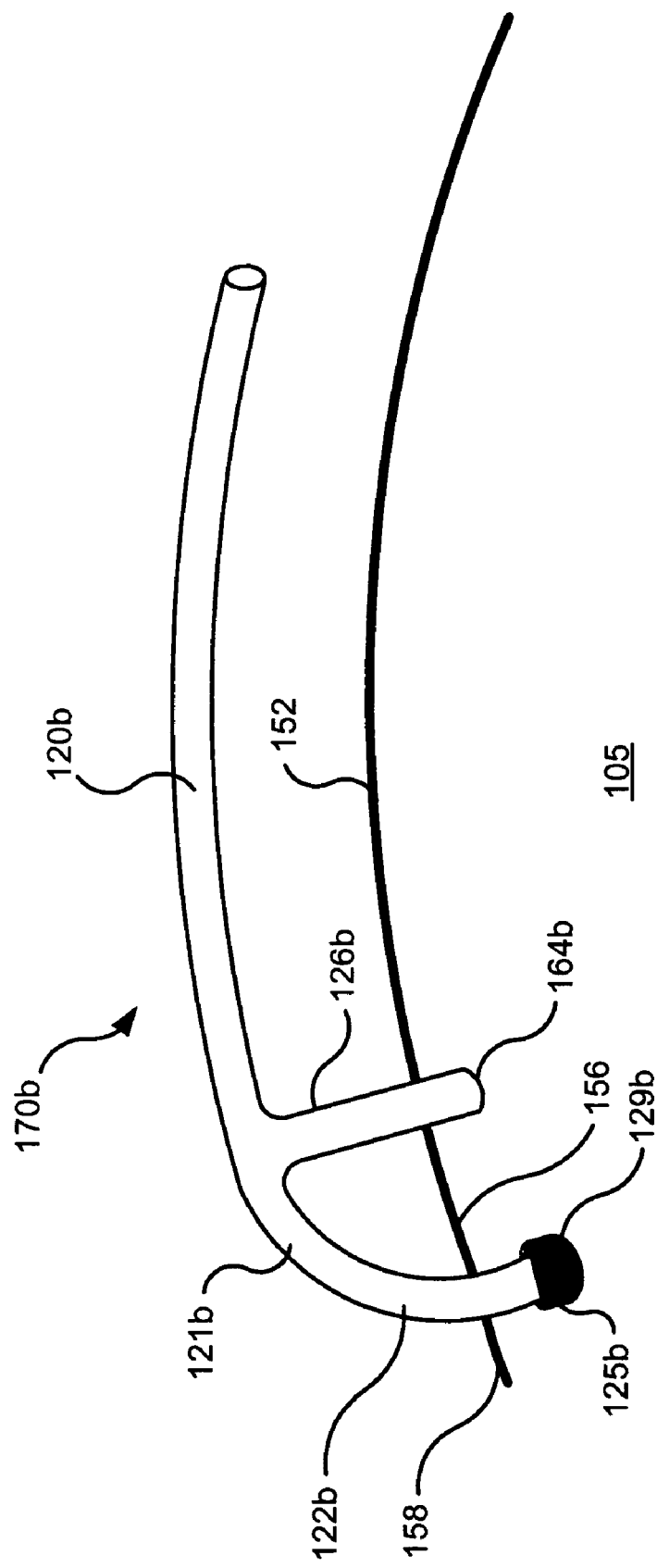
FIGS. 2A–2C illustrate various antenna configurations or connections in accordance with various embodiments of the present invention.
Figure 2B:
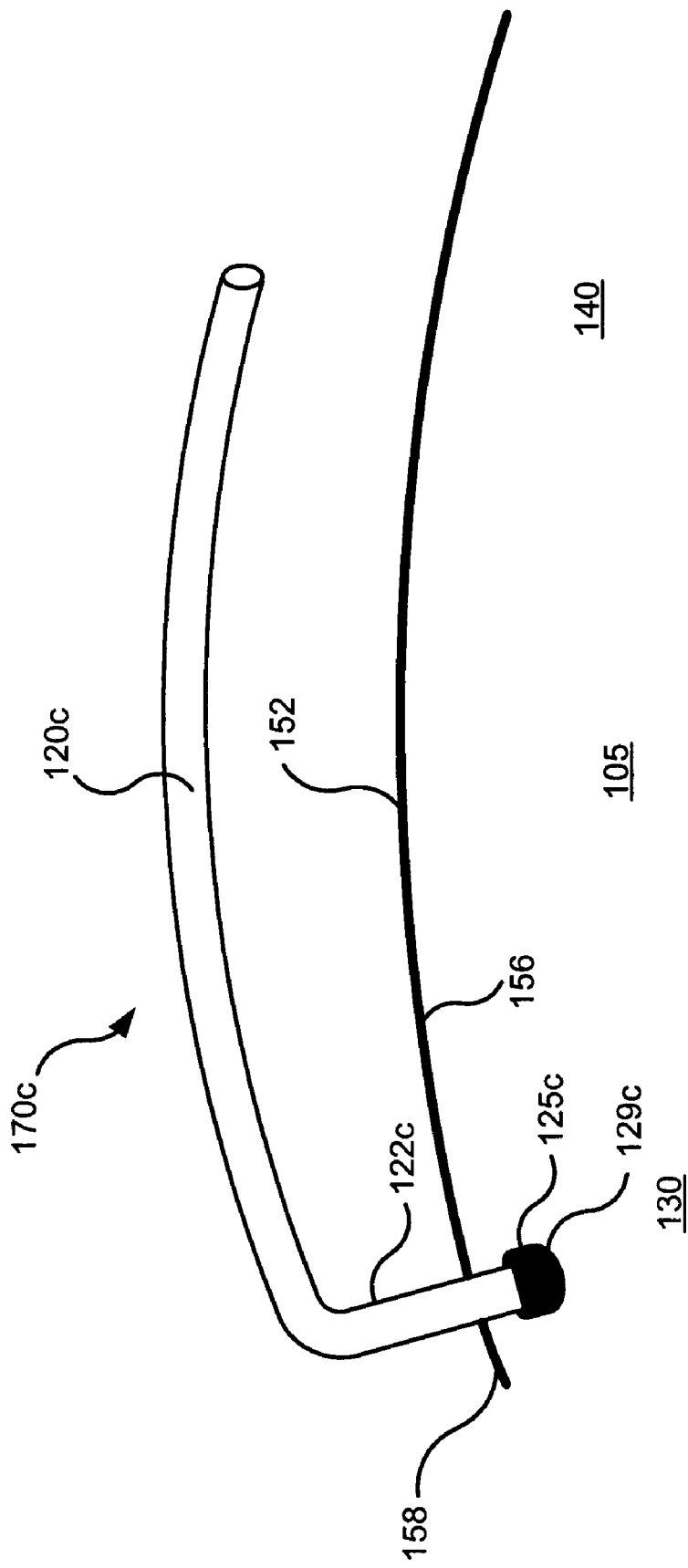
Figure 2C:
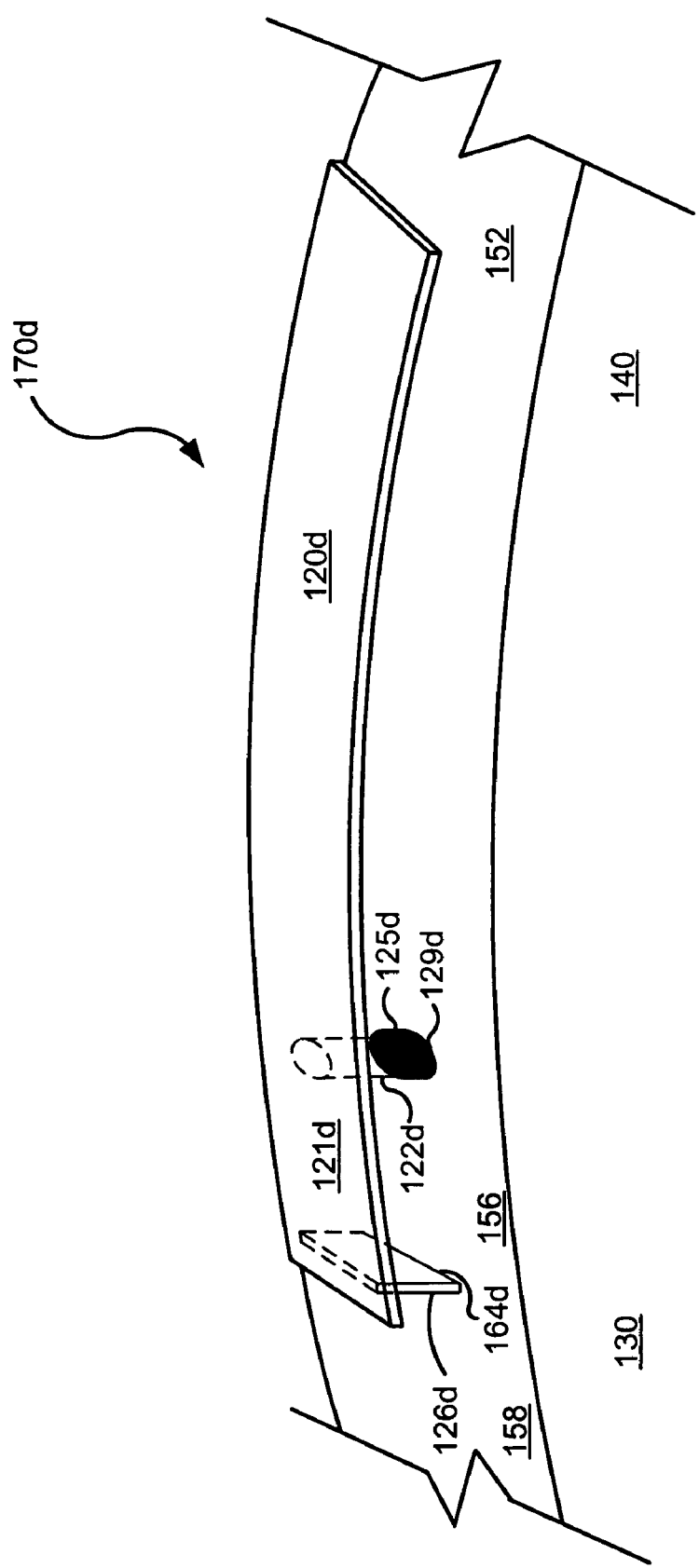

FIGS. 2A–2C depict just some of the many antennas that can be used. FIGS. 2A and 2B illustrate wire antennas, and FIG. 2C depicts a plate or ribbon cable antenna. Such wire and plate antennas can be either two-dimensional antennas with transmitting lengths, feed lines, and connector legs extending in a single plane, or as described in relation to FIG. 1B above, non-planar antennas. A plate antenna 170*d* of FIG. 2C includes a flattened metal piece forming a transmitting length 120*d* and a shunt arm 121*d*. Another flattened metal piece operates as a connector leg 126*d*, and can be located to tune the antenna by effectively adjusting the length of the shunt arm 121*d*. A Feed line 122*d* is a wire that is mechanically coupled to the transmitting length 120*d* and extends through the housing 105 as previously described. Further antenna types are discussed and illustrated in U.S. patent application Ser. No. 10/744,943 entitled "Radio Frequency Antenna in a Header of an Implantable Medical Device", and filed Dec. 22, 2003 by Rawat et. al. The entirety of the aforementioned patent application is incorporated herein in its entirety for all purposes.

Antennas in accordance with the present invention can extend from the header 130 and along the body 140 in a direction away from the header 130. In some cases, extending along the body 140 away from the header 130 is desirable because implementing such a design involves only minor changes in the design of the header 130. Further, the body 140 may offer a greater conductive surface, and thus it may improve antenna efficiency where a significant portion of the transmitting length 120 extends along the body 140. Alternatively, the antennas can extend from the body 140 and toward and/or along the outside of the header 130. Further, some embodiments of the present invention do not include a portion corresponding to the header 130, and thus the antenna is not implemented with any relation to the header 130.

Figure 3:
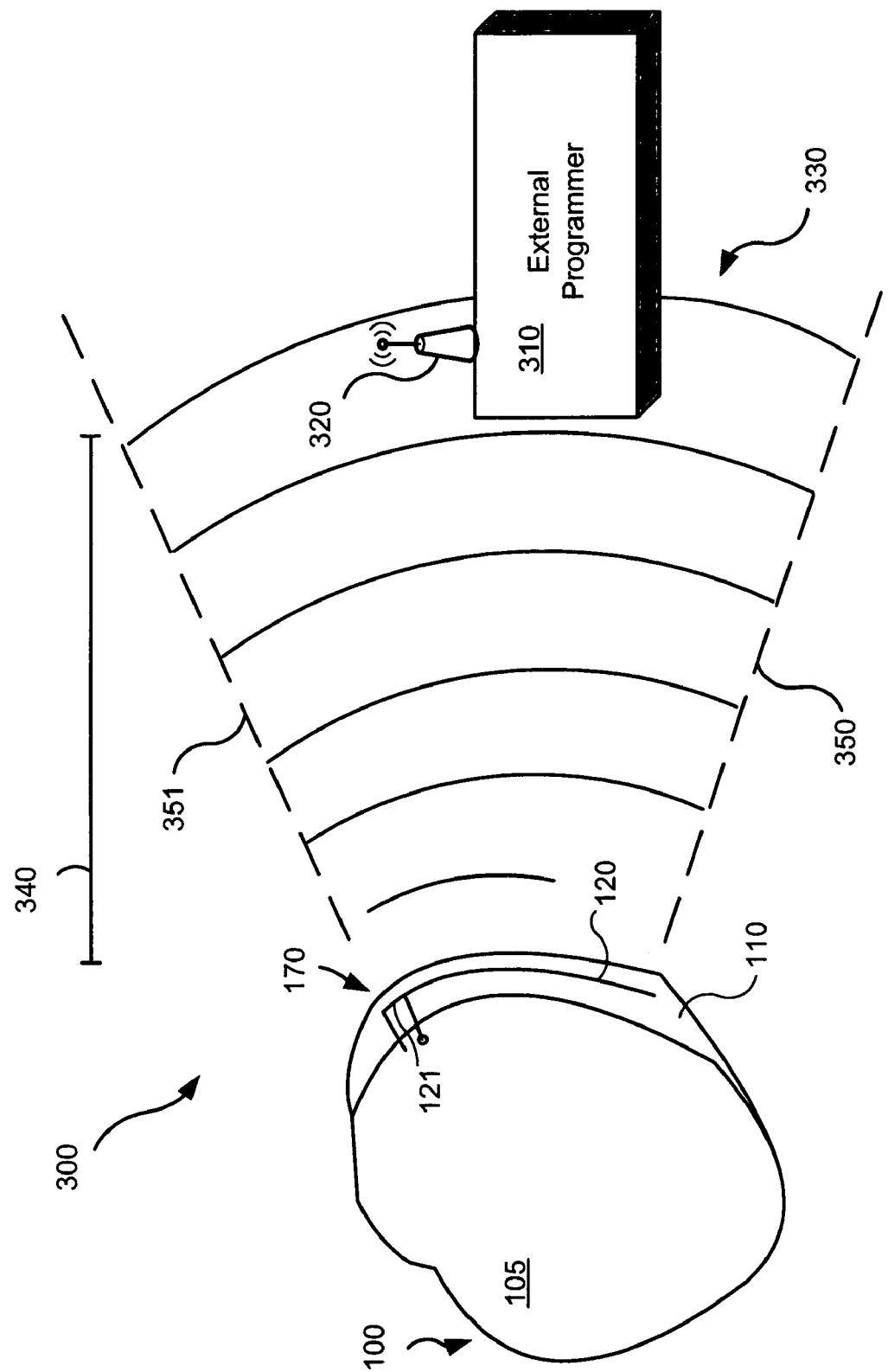
FIG. 3 depicts a system where communication is ongoing between an external programmer and a medical device in accordance with some embodiments of the present invention.

FIG. 3 shows a system 300 including the medical device 100 operating in relation to an external programmer 310 that includes an antenna 320. In operation, antenna 170 radiates RF waves 330 that extend out in a window or FOV depicted as a three-dimensional, conical region between dashed lines 350, 351. Because of the curvilinear shape of the transmitting length 120, the broadcast signal includes multiple polarizations which increases the FOV. Further, because of the efficiency of the antenna 170, a transmission distance 340 between the medical device 100 and the external programmer 310 can be increased.

By placing the antenna 170 along the side of the medical device 100, interference from the housing 105 is minimized for waves radiating in directions other than back toward the housing 105. Further, where the medical device 100 is deployed in a living being such that the shown side and the reverse side are oriented respectively toward the anterior and posterior of the living being, the radiation pattern 330 may be detected (depending upon the implantation depth of the medical device 100) from either the anterior or posterior of the human being without significant interference from the housing 105. Also, this reduces the implication of the orientation at which the medical device 100 can be placed. Mounting the antenna on the side also allows the feed line to utilize the same feed through used by other connections exiting the housing 105. Utilizing the same feed-through can greatly reduce the cost of manufacturing the medical device 100.

Figure 4:
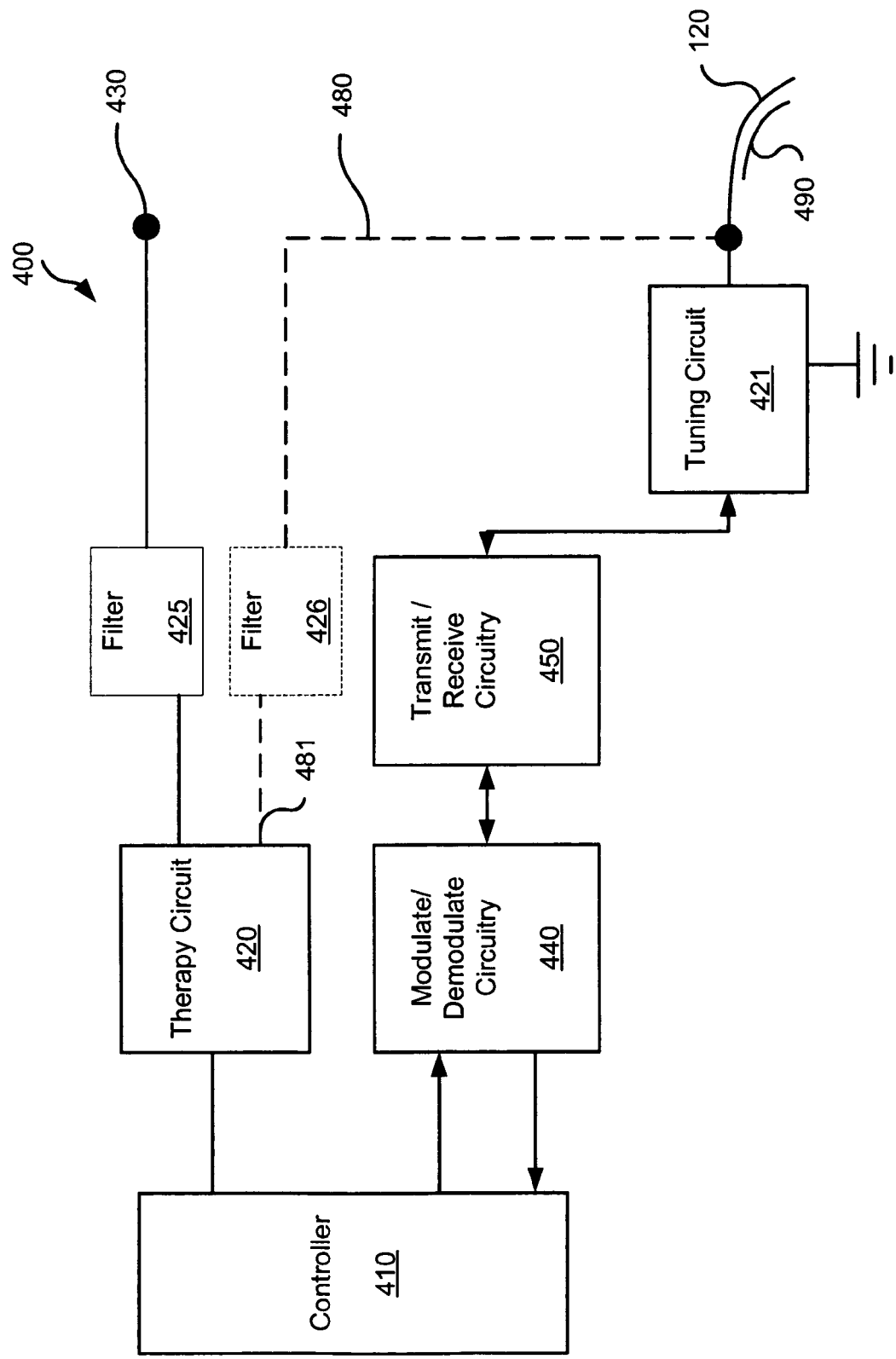
FIG. 4 is a block diagram of an exemplary electronic circuit incorporated within the device of FIG. 1.

FIG. 4 is a block diagram of an exemplary electronic circuit 400 incorporated within an exemplary medical device 100. The electronic circuit 400 includes a controller 410 that governs operation of various therapy circuitry 420 and modulation/demodulation circuitry 440. The therapy circuitry 420 can be any circuitry relevant to operation of a particular medical device in which it is included, and the controller 410 can be any controller capable of governing such therapy circuitry 420 and interacting with the modulation/demodulation circuitry 440. For example, the controller 410 can be a microprocessor, and the therapy circuitry 420 can be cardiac rhythm management circuitry.

The transmitting length 120 can include various transmission line characteristics denoted as element 490. Such transmission line effects can be reduced by adjusting the tuning circuit 421 that in some cases can include the shunt arm 121 grounded via a connector leg 426. The tuning circuit 421 can load the antenna with a varied amount of capacitance and/or inductance such that the effective length of the antenna is modified, and hence the resonant frequency of the antenna. As just some examples, it may be desirable for the antenna to resonate at 400–450 MHz, 862–870 MHz and/or 902–928 MHz. As other examples, the antenna can be designed to operate across a large frequency band such as, for example, from 862 to 928 MHz. In one particular embodiment, the antenna is designed to resonate at 916.5 MHz and to operate across a frequency band from 862–928 MHz. In particular cases, the antenna can be designed to work at both ISM (902–928 MHz) and SRD (862–870 MHz) bands.

In some cases, an alternative tuning circuit 421 can be used that is comprised of other variable inductive and/or capacitive elements to form a lumped matching network. Whether impedance matching is performed using a shunt arm, and/or a lumped matching network, a high degree of electrical matching can be achieved when compared to other circumferential and loop antennas. Tuning circuit 421 can be modified depending on a number of factors including whether the antenna is a monopole or a dipole, or whether the antenna is an inverted-F antenna. In some cases, tuning circuit 421 is implemented using shunt arm 121 and connector leg 126. Other elements and/or combinations thereof can be used. Additional information discussing impedance matching can be found in R. W. P. King et al., "Transmission-line missile antennas," IRE Transactions on Antennas and Propagation, vol. AP-42, pp. 88–90, January 1960. The entirety of the aforementioned reference is incorporated herein by reference for all purposes.

The therapy circuitry 420 is electrically coupled to one or more therapy leads 430 via one or more filters 425 that serve to isolate therapy circuitry 420 from any RF signals that may be picked up by the lead. In some cases, filter 425 is a low-pass filter or a notch filter such as a choke. Further, in the case where the transmitting length 120 is to be used as a therapy lead, it is connected to therapy circuitry by a filter 426 that operates similar to isolate the therapy circuitry 420 from any RF signals being received and/or transmitted on the transmitting length 120. As this is optional, connection of the transmitting length 120 as a therapy lead is indicated by dashed lines 480, 481.

The controller 410 also outputs and receives the data contained in the modulated carrier generated or received via the transmitting length 120, the transmit/receive circuitry 450, and the modulation/demodulation circuitry 440. The aforementioned circuitry 440, 450 includes an RF transmitter and receiver that are connected by a transmit/receive switch the transmitting length 120 via feed line.

Although the present invention has been described with reference to preferred embodiments, persons skilled in the art will recognize that changes may be made in form and detail without departing from the spirit and scope of the invention.

We claim:

1. An implantable medical device comprising:
    a housing surrounding at least one circuit;
    an inverted-f antenna extending along the housing, the antenna electrically coupled to the at least one circuit; and
    a coating covering at least a portion of the housing and at least a portion of the inverted-f antenna.

2. The device of claim 1 wherein the housing is formed of a conductive material.

3. The device of claim 2 wherein a portion of the inverted-f antenna extends along an outer section of the housing.

4. The device of claim 3 wherein the portion of the inverted-f antenna extending along the outer section of the housing is curvilinear in shape and approximately follows the outer section of the housing.

5. The device of claim 4 wherein the curvilinear portion of the inverted-f antenna is operable to broadcast a signal with multiple polarizations.

6. The device of claim 1 wherein the inverted-f antenna includes a shunt arm, and wherein the shunt arm is shorted to the housing.

7. The device of claim 1 wherein the inverted-f antenna includes a shunt arm, and wherein the shunt arm is capacitively coupled to the housing.

8. The device of claim 1 wherein a portion of the inverted-f antenna operates as both an electrode and as a wireless transmission element.

9. The device of claim 8 wherein the implantable medical device is a pacemaker, and wherein the portion of the inverted-f antenna is operable in conjunction with other electrodes associated with the pacemaker to generate an electrocardiogram.

10. The device of claim 1 wherein the housing includes a header, wherein a portion of the inverted-f antenna extends along an outer section of the housing away from the header.

11. The device of claim 10, wherein a leg of the inverted-f antenna is coupled to the housing at a location away from the header.

12. The device of claim 1 wherein at least a portion of the inverted-f antenna is encapsulated in a polymer.

13. The device of claim 1 wherein the coating comprises a polymer.

14. The device of claim 13 wherein a dielectric constant of the polymer and a thickness of the polymer measured from the housing to a location on the inverted-f antenna at least partially defines an operational characteristic of the inverted-f antenna.

15. The device of claim 1 wherein the inverted-f antenna is tailored for dual frequency band operation.

16. The device of claim 15 wherein one of the frequencies included in the dual frequency band operation is selected for use in a first geopolitical region, and the other of the frequencies included in the dual frequency band operation is selected for use in a second geopolitical region.

17. The device of claim 1 wherein the inverted-f antenna is a three-dimensional inverted-f antenna.

18. The device of claim 17 wherein the three-dimensional inverted-f antenna comprises wire, and wherein the wire includes a metal selected from a group consisting of: platinum, stainless steel, irridium, niobium, gold and silver core stainless steel.

19. The device of claim 1 wherein the housing includes a side, a front, and a back; wherein deployment of the implantable medical device includes placing the implantable medical device within a human being such that the front faces the anterior of the human being and the back faces the posterior of the human being, and wherein the inverted-f antenna is disposed along the side of the implantable medical device.

20. An implantable medical device, the device comprising:
    a means for containing an electrical circuit, wherein the means for containing includes a side, a front and a back, and wherein the front is deployed toward the anterior of a human body when the implantable medical device is deployed;
    a means for transmitting and receiving wireless information, wherein the means for transmitting and receiving wireless information extends along less than one half of the side of the means for containing; and
    a human body compatible means for protecting the exterior of the implantable medical device.

21. The implantable medical device of claim 20 wherein the means for transmitting and receiving wireless information is an inverted-f antenna.

22. The implantable medical device of claim 21 wherein the inverted-f antenna is a non-planar inverted-f antenna.

23. The implantable medical device of claim 20 wherein the means for transmitting and receiving wireless information includes an antenna and an antenna tuning circuit for matching the impedance of the antenna to the electrical circuit at a specified frequency of the radio-frequency carrier.

24. The implantable medical device of claim 23 wherein the antenna tuning circuit comprises a variable tuning capacitor for adjusting the resonant frequency of the antenna.

25. The implantable medical device of claim 20 wherein the electrical circuit includes a cardiac rhythm management circuit electrically coupled to one or more electrodes adapted for disposition within or near the heart by one or more therapy leads.

26. An implantable cardiac rhythm device comprising a housing including a header, the housing surrounding at least one electrical circuit, and an antenna including a feed line electrically coupled to the electrical circuit, wherein a length of the antenna extends along an outer surface of the housing away from the header.

27. The implantable cardiac device of claim 26 wherein the antenna is an inverted-f antenna.

28. The implantable cardiac device of claim 26 wherein the housing includes a feed through, and wherein the feed line passes through the feed through.

29. The implantable cardiac device of claim 26 wherein the at least one electrical circuit is operable to perform a function selected from the group consisting of: receive a signal from the antenna, and transmit a signal to the antenna.

30. The implantable cardiac device of claim 26 wherein the housing is conductive, wherein the length of the antenna extending along the outer surface of the housing is encapsulated in a coating, and wherein the coating forms a dielectric barrier between the conductive housing and the length of the antenna extending along the outer surface of the housing.

31. The implantable cardiac device of claim 30 wherein the distance from the antenna to the conductive housing is approximately equal along the length of the antenna extending along the outer surface of the housing.

32. The implantable cardiac device of claim 27 wherein the device is an implantable pacemaker; wherein the housing includes a side, a front, and a back; wherein deployment of the implantable pacemaker includes placing the implantable pacemaker within a human being such that the front faces the anterior of the human being and the back faces the posterior of the human being, and wherein the inverted-f antenna is disposed along the side of the implantable pacemaker.

33. A method for manufacturing an implanted medical device, the method comprising:

providing a conductive housing surrounding at least one electrical circuit, wherein the conductive housing includes a front, a back, and a side, and wherein the implantable medical device when deployed within a living being is oriented such that the front faces the anterior of the living being and the back faces the posterior of the living being;

providing an antenna, wherein the antenna includes a feed line and a shunt line, wherein the at least one electrical circuit is electrically coupled to the feed line;

extending a dielectric compartment along the side of the conductive housing; and embedding the antenna within the dielectric compartment, wherein the antenna extends along and displaced from the side of the conductive housing.

34. The method of claim 33 wherein the conductive housing includes a side, a front, and a back; wherein the deployed medical device is disposed within the living being such that the front faces the anterior of the living being and the back faces the posterior of the living being; wherein the length of the antenna extends along the side of the housing; and wherein placing an external programmer in a location selected from a group consisting of: a location displaced from the anterior of the living being, a location displaced from the posterior of the living being, and a location displaced from the side of the living being.

35. A method for programming a medical device, the method comprising:

programming the implantable medical device using an external programmer, wherein the implantable medical device includes an inverted-F antenna, and wherein programming the implantable medical device includes disposing the implantable medical device relative to the external programmer at a distance sufficient to eliminate the need for sterilization of any portion of the external programmer.

36. The method of claim 35 wherein programming the implantable medical device is performed at a frequency selected from the group consisting of: about 400–450 MHz, about 862–870 MHz, and about 902–928 MHz.

* * * * *

UNITED STATES PATENT AND TRADEMARK OFFICE
CERTIFICATE OF CORRECTION

PATENT NO.        : 7,047,076 B1
APPLICATION NO.   : 10/808060
DATED             : May 16, 2006
INVENTOR(S)       : Zhifang Li et al.

Page 1 of 1

It is certified that error appears in the above-identified patent and that said Letters Patent is hereby corrected as shown below:

TITLE PAGE, ITEM (63)
Related U.S. Application Data Section

The Related U.S. Application Data Section should read:

Continuation in part of application No. ~~10/634,233~~ 10/744,943, filed on ~~Aug. 5~~ Dec. 22, 2003, ~~now Pat. No. 6,809,701~~ and a continuation in part of application No. 10/634,233 ~~10/744,943~~, filed on Aug. 5 ~~Dec. 22~~, 2003, now Pat. No. 6,809,701, which is a continuation of application No. 10/252,494, filed on Sep. 23, 2002, now Pat. No. 6,614,406 which is a continuation of application No. 09/921,653, filed on Aug. 3, 2001, now Pat. No. 6,456,256.

Signed and Sealed this

Nineteenth Day of December, 2006

JON W. DUDAS
*Director of the United States Patent and Trademark Office*